(12) United States Patent
Mitra et al.

(10) Patent No.: US 7,785,637 B2
(45) Date of Patent: Aug. 31, 2010

(54) HERBAL COMPOSITION FOR MAINTAINING/CARING THE SKIN AROUND THE EYE, METHODS OF PREPARING THE SAME AND USES THEREOF

(75) Inventors: Shankar Kumar Mitra, Bangalore (IN); Ekta Saxena, Bangalore (IN); Uddagiri Venkanna Babu, Bangalore (IN)

(73) Assignee: Himalaya Global Holdings Ltd., Grand Cayman, British West Indies (KY)

( * ) Notice: Subject to any disclaimer, the term of this patent is extended or adjusted under 35 U.S.C. 154(b) by 0 days.

(21) Appl. No.: 11/811,173

(22) Filed: Jun. 8, 2007

(65) Prior Publication Data

US 2008/0081085 A1 Apr. 3, 2008

(51) Int. Cl.
*A61K 36/00* (2006.01)
(52) U.S. Cl. .................................... 424/725
(58) Field of Classification Search ........................ None
See application file for complete search history.

(56) References Cited

U.S. PATENT DOCUMENTS

| | | |
|---|---|---|
| 6,235,721 B1 | 5/2001 | Ghosal |
| 6,406,682 B1 | 6/2002 | Martin et al. |
| 6,641,845 B1 | 11/2003 | Kyrou et al. |
| 6,682,763 B2 | 1/2004 | Kuno et al. |
| 6,699,463 B2 | 3/2004 | Chaudhuri |
| 2004/0115286 A1 | 6/2004 | Lee et al. |
| 2005/0089589 A1 | 4/2005 | Chaudhuri et al. |

FOREIGN PATENT DOCUMENTS

JP  06-329545  * 11/1994

OTHER PUBLICATIONS

Katelaris et al. 2006. MJA. vol. 185. No. 9. pp. 517-522.*
Revilla et al. 1998. J. Agric Food Chem. 46; pp. 4592-4597.*
Narayan Manandhar. Plants and People of Nepal. 2002. pp. 153-154.*
Asmawi et al. Anti-inflammatory Activities of Emblica Officinalis Gaertn Leaf Extracts. J.Pharm. Pharmacol. Jun. 1993; 45(6): Abstract.*
Gupta, R. In *Medicinal and Aromatic Plants of Bhandal Range, Churah Forest Division, Chamba District, Himachal Pradesh*, 1971 J. Bombay Nat. Hist. Soc., 68:791-803.
Jain and Gupta 1962 "Isolation of Bergenin from *Saxifraga Lingulata* Wall" *J Indian Chem Soc* 39:559-60.
Shah et al. 1972 "Pharmacognistic Study of Pashanbhed, Part 1", *Quart J Drud Drug Res* 12:1882-1893.
The Wealth of India : A Dictionary of Indian Raw Materials & Industrial Products: First Supplement Series (Raw Materials) vol. -3: Ca-Ci. New Delhi, National Institute of Science Communication and Information Resources, 1992.
The Wealth of India : A Dictionary of Indian Raw Materials & Industrial Products: First Supplement Series (Raw Materials) vol. -2: B. New Delhi, National Institute of Science Communication and Information Resources, 1992, pp. 119-120.

* cited by examiner

*Primary Examiner*—Christopher R Tate
*Assistant Examiner*—Melenie McCormick
(74) *Attorney, Agent, or Firm*—Knobbe Martens Olson & Bear LLP

(57) ABSTRACT

Disclosed is a novel herbal composition for maintaining/caring the skin around the eye, the composition comprising extracts of *Saxifraga ligulata* syn. *Bergenia ligulata*, *Cipadessa baccifera* and *Emblica officinalis* and cosmeceutical excipients thereof. Also disclosed is a method of extraction, delivery system comprising the same and use thereof.

8 Claims, 10 Drawing Sheets

HERBAL COMPOSITION FOR MAINTAINING/CARING THE SKIN AROUND THE EYE, METHODS OF PREPARING THE SAME AND USES THEREOF

CROSS-REFERENCE TO RELATED APPLICATIONS

This application claims the benefit of Indian Application No. 2151/DEL/2006, filed Sep. 28, 2006.

FIELD OF THE INVENTION

In general this invention relates to the filed of cosmecuticals. More specifically the present invention provides a novel herbal skinceutical composition to maintain and improve skin health especially for delicate skin around the eyes comprising the extracts of *Saxifraga ligulata, Cipadessa baccifera* and *Emblica officinalis*, method for preparing the same and use thereof.

BACKGROUND OF THE INVENTION

The Eye care cosmeceutical products are one of the top selling cosmetics in the world. The skin around the eye is very thin and when blood passes through the large veins close to the surface of the skin it can produce a bluish tint. The more transparent the skin, which is also an inherited trait, the darker the circles appear.

Hyperpigmentation (a high amount of melanin in the skin) is often the culprit for dark circles under the eyes, as is engorged blood vessels in the thin skin under the eye. This is especially common for the fair-skinned people. Also fatigue, excessive sun exposure, dehydration, and medical conditions related to renal, thyroid and even genetics could cause dark circles to appear.

The fine lines at the corner of one's eyes are commonly referred to as "crow's feet". This area has fewer oil glands than rest of the face, and is susceptible to extra dryness and formation of wrinkles.

Puffiness of eyes and eye bags are two different kinds of conditions. While fluid retention is the main cause of puffy eyes, a common occurrence in the morning, as fluid builds up while sleeping and baggy eyes are the result of accumulated fat in the eye area. Over time, the septum surrounding the eyeball socket weakens, which causes the outer layer of fat within the socket to sink forward—resulting in pouches, or bags.

area. Over time, the septum surrounding the eyeball socket weakens, which causes the outer layer of fat within the socket to sink forward—resulting in pouches, or bags.

Tyrosinase, a single-chain glycoprotein enzyme essential to pigment formation in mammals, is specifically localized in melanocytes, which occur primarily in the skin, hair bulbs, and eyes. Tyrosinase, the rate-limiting enzyme in melanin synthesis, is expressed specifically in pigment-producing cells. Tyrosinase converts tyrosine to dihydroxyphenylalanine (DOPA) and then to dopaquinone. Subsequently, dopaquinone is converted to dopachrome, through auto-oxidation, and finally to dihydroxyindole or dihydroxyindole-2-carboxylic acid (DHICA) to form melanin (brown-black pigment). Tyrosinase enzyme inhibitors have a greater role to play for treating hyper pigmentation of the skin around eyes.

Hyaluronic Acid (HA), a natural glycosaminoglycan biopolymer, is present in the tissues. It has an enormous water binding capacity (up to 1,000 times its weight) and it forms high viscosity hydrated polymers. More than 50% of the total amount of body HA is present in skin (in dermis and epidermis). Hyaluronic acid is a basic building block of the dermis. It stabilizes the intercellular structures of connective tissues and forms the elastoviscous fluid matrix in which collagen and elastin fibers are embedded. It also promotes the renewal of keratinocytes and its ability to retain water helps in proper hydration of the skin. The amount of HA in the skin decreases with aging and photo aging process. Hyaluronidase is an enzyme that degrades HA resulting in reduced dermal hydration, disorganization of collagen and elastin fibers and increased skin wrinkling and folding. Hyaluronidase Inhibitors are known to have potential benefits in preventing and treating crow's feet type of fine line wrinkles.

The free radical damage of the skin around the eyes causing inflammation and reddening of eye can be treated with the addition of antioxidants in eye creams. Antioxidants are found naturally in the body and in plants such as fruits and vegetables. Common antioxidants include vitamin A, vitamin C, vitamin E, and certain compounds called carotenoids (e.g., lutein and beta-carotene). Antioxidants help to prevent the destruction of cells by bonding with free radicals. Free radicals are atoms or groups of atoms with an odd (unpaired) number of electrons and can be formed when oxygen interacts with certain molecules. Free radicals are often generated due to pollution and stress.

All the above literature cited information suggests the importance of tyrosinase enzyme inhibitors, hyaluronidase enzyme inhibitors and antioxidants as active ingredients in the formulation of under eye care cosmeceutical preparations for prevention and treatment of dark circles, puffiness of eyes, eye bags and fine wrinkles around the eyes etc. for human beings.

U.S. Pat. No. 6,682,763 to Kuno et al. describes the preparation of Skin-beautifying agent, anti-aging agent for the skin, whitening agent and external agent for the skin using multi herbal composition comprising *Saxifraga stronifera* Meerburg, marshmallow, *Angelica keiskei Koidz, Artemisia capillaries herba*, nettle, philodendron bark, *Hypericum erectum, lonicerae flos, Salvia officinalis, lithospermum* roots, white birch, *Sapindus mukurossi Gaertn*, etc.

U.S. Pat. No. 6,641,845 to Kyrou et al. demonstrates the preparation of skin whitening composition comprising bearberry and tetrahydrocurcumin.

U.S. Pat. No. 6,406,682 to Martin et al. teaches the use of *Saxifraga* extracts for artificial tanning of human skin.

U.S. Patent Application No. 20040115286 to Lee Kang Tae et al. discloses the preparation of herbal composition comprising the extract of *Bergenia emeiensis* for remedying skin wrinkles.

U.S. Patent Application No. 20050089589 to Chaudhuri et al. describes the use of *Emblica officinalis* extract as skin lightening agent.

U.S. Pat. No. 6,699,463 to Chaudhuri et al. discloses the preparation photostable sunscreen composition comprising *Emblica officinalis* extract as one of the antioxidant agent.

U.S. Pat. No. 6,235,721 to Ghosal et al. demonstrates a process for the stabilization of Vitamin C content as antioxidant from *Emblica officinalis*.

SUMMARY OF THE INVENTION

It is a principal aspect of the present invention to provide a novel herbal composition for maintaining skin around the eyes, wherein said composition comprises the extracts of

*Saxifraga ligulata* syn. *Bergenia ligulata*, *Cipadessa baccifera* and *Emblica officinalis* and cosmeceutically acceptable excipients.

In accordance with another aspect of the present invention, a novel herbal composition is provided, which is capable of preventing and treating under eye dark circles, under eye wrinkles, under eye bags, a free radical damage of the skin around eye, hyper pigmentation around the eye, inflammation or puffiness around the eye, due to age, stress, insomnia, allergy, dehydration and genetically inherited disorders or other problems related to the same.

It is another aspect of the present invention to provide a novel herbal composition, wherein said composition is capable of inhibiting the enzyme Tyrosinase that can cause irregular skin coloring. Further said herbal composition inhibits the production of Hyaluronidase enzyme, which helps to achieve the reduction of free radicals.

It is yet another aspect of the present invention to provide a novel herbal composition comprising the extract of *Saxifraga ligulata* syn. *Bergenia ligulata* and cosmeceutically acceptable excipients, wherein said composition is capable of inhibiting the enzyme Tyrosinase.

In accordance with yet another aspect of the present invention, there is provided a novel herbal composition comprising the extract of *Cipadessa baccifera*, wherein said composition is capable of inhibiting Hyaluronidase enzyme.

In accordance with yet another aspect of the present invention, there is provided a novel herbal composition comprising the extract of *Emblica officinalis*, wherein said composition effectively acts as an antioxidant and is capable of preventing free radical damage of the skin around eye.

In accordance with further aspect of the present invention, there is provided a composition, wherein said composition is effectively used for skin lightening under eye.

In accordance with yet another aspect of the present invention, there is provided a process to prepare solvent extract of said plants *Saxifraga ligulata* syn. *Bergenia ligulata*, *Emblica officinalis* and *Cipadessa baccifera*, employing a solvent selected from the group comprising n-hexane, dichloromethane, chloroform, ethyl acetate, acetone, methanol, ethyl alcohol and water or any combination thereof.

In accordance with yet another aspect of the present invention, the solvent extract is prepared using any part of said plants, preferably rhizomes of *Saxifraga ligulata*, fruits of *Emblica officinalis* and aerial parts of *Cipadessa baccifera*.

According to another aspect of the present invention, there is provided a novel herbal composition comprising the extract of *Cipadessa baccifera*, wherein said extract is obtained employing an aqueous solvent viz. water, either alone or in any combination of alcohol.

According to another aspect of the present invention, there is provided a novel herbal composition comprising the extract of *Saxifraga ligulata*, wherein said extract is obtained employing an organic solvent viz. methanol, either alone or in any combination of other organic solvents.

According to another aspect of the present invention, there is provided a novel herbal composition comprising the extract of *Emblica officinalis*, wherein said extract is obtained employing an organic solvent viz. methanol, either alone or in any combination of other organic solvents.

In accordance with another aspect of the present invention, there is provided a novel herbal composition, wherein the composition is intended for topical application in human beings.

In accordance with one preferred embodiment of the present invention, there is provided a herbal composition for maintaining skin around the eyes, wherein said composition comprises extracts of *Saxifraga ligulata* syn. *Bergenia ligulata*, *Cipadessa baccifera* and *Emblica officinalis* and cosmeceutically acceptable excipients.

In accordance with yet another preferred embodiment of the present invention, there is provided a novel herbal composition, wherein said herbal extract composition comprises water extract of *Cipadessa baccifera*, methanol extract of *Emblica officinalis* and methanol extract of *Saxifraga ligulata* in any combination, preferably in the ratio of 34:21:45.

In accordance with still another preferred embodiment of the present invention, there is provided a novel herbal composition, wherein said composition comprises chromatographic fraction eluted with Chlroform:Methanol (50:50) from the methanol extract of *Saxifraga ligulata*.

In accordance with still another embodiment of the present invention, the topical formulation comprises from 0.1 to 10% of the herbal extract composition, wherein said formulation may be cream, gel, lotion or any other topical formulation.

In accordance with still another embodiment of the present invention, there is provided a process for preparing the extracts of *Saxifraga ligulata* syn. *Bergenia ligulata*, *Emblica officinalis* and *Cipadessa baccifera*, wherein said extracts are obtained employing percolation method or hot soxhalation method or direct extraction method.

In accordance with still another embodiment of the present invention, there is provided a method for preparing said composition employing extract of *Saxifraga ligulata* syn. *Bergenia ligulata*, *Emblica officinalis* and *Cipadessa baccifera*, wherein said method comprises extracting plant extract from said plants by hot soxhalation, filtering the plant extract, concentrating the plant extract to dryness on rotatory evaporator or on steam bath at optimum temperature and producing a herbal composition employing said dry extract and a cosmeceutically acceptable carrier.

In accordance with still another embodiment of the present invention, there is provided a method for preparing said composition employing extract of *Saxifraga ligulata* syn. *Bergenia ligulata*, *Emblica officinalis* and *Cipadessa baccifera*, wherein said method comprises extracting plant extract from said plants by percolation, filtering the plant extract, concentrating the plant extract to dryness on rotatory evaporator or on steam bath at optimum temperature and producing a herbal composition employing said dry extract and a cosmeceutically acceptable carrier.

In accordance with still another embodiment of the present invention, there is provided a method of producing a bioactive fraction by solvent fractionation of methanol extract from the plant *Saxifraga ligulata*, wherein the solvent is Chloroform:Methanol in ratio of 80:20, preferably Chloroform:Methanol in ratio of 50:50. Further, the prepared fraction is a potent Tyrosinase enzyme inhibitor.

In accordance with yet another embodiment of the present invention, there is provided a method of producing a bioactive fraction by column chromatography of methanol extract from the plant *Saxifraga ligulata*, wherein the column is prepared from silica gel as adsorbent and wherein said bioactive fraction is obtained from chloroform: methanol (50:50) eluted fraction.

In accordance with further embodiment of the present invention, there is provided a method of producing a bioactive fraction directly from the plant material *Saxifraga ligulata*, wherein the plant material is extracted with chloroform:methanol (80:20) followed by chloroform:methanol (50:50) solvent mixture.

Further, the bioactive fraction from *Saxifraga ligulata* comprises up to 45% of said under eye cream composition according to the present invention.

In accordance with still another embodiment of the present invention, there is provided a method of treating patients suffering from wrinkles under the eye, laxity of the muscles below the eye or dark black circles around the eye with under eye cream.

BRIEF DESCRIPTION OF THE DRAWINGS

Further objects of the present invention together with additional features contributing thereto and advantages accruing there from will be apparent from the description of preferred embodiments of the present invention which are shown in the accompanying drawing figures.

DETAILED DESCRIPTION OF THE PREFERRED EMBODIMENT

The present invention involves the selection of various herbs and obtaining extract by subjecting the same to solvent extraction and screening of these extracts for tyrosinase and hyaluronidase enzymes inhibitory activities and antioxidant activity in vitro. The invention also involves preparation of a cosmeceutical composition using the effective herbal extracts in a particular ratio and other cosmeceutically acceptable carriers and evaluation of its skin lightening activity in rats. The present cosmeceutical composition is effective for prevention and treatment of under eye dark circles, under eye wrinkles, under eye bags, free radical damage around the skin of eye, hyper pigmentation around the eye, inflammation or puffiness around the eye in human beings.

*Saxifraga ligulata* syn. *Bergenia ligulata*: A perennial herb with stout rootstock, found in the temperate Himalayas between altitudes of 900 and 3,000 m. Leaves variable, 5-35 cm long, coarsely hairy, sparsely hairy to glabrous, broadly obovate or elliptic; flowers white, pink or purple, in long cymose panicles.

The dried rhizomes constitute the drug Paashaanabheda. The name Paashaanabheda is attributed to about a dozen plants belonging to different genera, but the drug in the Indian markets mainly consists of two closely related herbs (i) *B. ciliata F. ciliata* syn. *Saxifraga ligulata* auct, in part, non Wall.; *S. ligulata* Wall. var. *ciliata* (Royle) Hook. f. & Thoms.

The rhizome of *S. ligulata* contains an active principle, bergenin (0.6%), gallic acid, glucose (5.6%), mucilage and wax. The presence of β-sitosterol and four flavonoids is also reported. The rhizome is a source of tannin (14.2-16.3%) and of a dye (Jain & Gupta, 1962 *J Indian Chem Soc* 39:559; Gupta, 1971 *J Bombay Nat Hist Soc* 68:791; Bahl et al. 1974 *Indian J Chem* 12:1038; Shah et al. loc. cit.; Sarin & Kapoor, loc. cit.).

*Emblica officinalis* Gaertn. Syn. *Phyllanthus emblica* Linn. (Amla) belongs to the family Euphorbiaceae and is a small or medium-sized deciduous tree with smooth, greenish grey exfoliating bark. Leaves are feathery with small narrowly oblong, pinnately arranged leaflets. Fruits are depressed-globose, ½-1 inch in diameter, fleshy and obscurely 6-lobed, containing trigonous seeds.

Amla fruit is probably the richest known natural source of vitamin C. The fruit juice contains nearly 20 times as much vitamin C as orange juice and a single fruit is equal in antiscorbutic value to one or two oranges. A tannin containing gallic acid, ellagic acid and glucose in its molecule and naturally present in the fruit prevents or retards the oxidation of the vitamin and renders the fruit a valuable antiscorbutic in the fresh as well as dry condition.

*Cipadessa baccifera* (Roth) Miq. Syn. *C. fruticosa* Blume, a genus of shrubs or small trees belongs to the family Meliaceae and distributed in the Indo-Malaysian region. *C. baccifera* is a much-branched shrub up to 2.5 m in height with imparipinnate leaves, elliptic lanceolate leaflets, small white flowers in axillary corymbose panicles, and red globose berries, commonly found in parts of South India. The roots are used against tapeworms. The leaves make a poor fodder. The wood is used as fuel (Bressers, 27; Laurie, 1945 *Indian For. Leafl.* 82:13).

Example 1

Preparation of *Saxifraga ligulata* Extract by Percolation Method

The shade dried rhizomes of *Saxifraga ligulata* were pulverized to coarse powder and about 1 Kg each of powdered material placed in different percolators and the material was soaked in n-hexane, dichloromethane, chloroform, ethyl acetate, acetone, ethanol, methanol and water at room temperature for 24 h to 48 h then plant extracts were drained out from the percolator and filtered through Whatmann no. 1 filter paper. The percolation of the residual material was again carried out with respective solvents and the combined solvent extract was concentrated to dryness on rotatory evaporator or on steam bath at optimum temperature and under reduced pressure.

Example 2

Preparation of *Saxifraga ligulata* Extract by Hot-Soxlation Method

The shade dried rhizomes of *Saxifraga ligulata* were pulverized to coarse powder and about 1 Kg each of the powdered material subjected to hot-soxlation in different soxhalate apparatus using solvents n-hexane, dichloromethane, chloroform, ethyl acetate, acetone, ethanol and methanol at optimum temperature until extraction was completed, then plant extracts were filtered through Whatmann no. 1 filter paper and concentrated to dryness on rotatory evaporator or on steam bath at optimum temperature. All extracts were qualitatively similar to extracts prepared by percolation method.

Example 3

Solvent-Solvent Fractionation of *Saxifraga ligulata* Methanol Extract

About 10 g of methanolic extract of *Saxifraga ligulata* was macerated with n-hexane, n-hexane-chloroform (1:1), chloroform, chloroform-methanol (90:10), chloroform-methanol (80:20), chloroform-methanol (70:30), chloroform-methanol (50:50), chloroform-methanol (25:75) and methanol successively to yield hexane fraction (0.2 g), n-hexane-chloroform (50:50) fraction (0.34 g), chloroform fraction (0.46), chloroform-methanol (90:10) fraction (0.8 g), chloroform-methanol (80:20) fraction (1.2 g) (TR-1), chloroform-methanol (70:30) fraction (1.1 g) (TR-2), chloroform-methanol (50:50) fraction (2.8 g) (TR-11), chloroform-methanol (25:75) (TR-3) fraction (1.5 g) and methanol fraction (1.4 g).

Example 4

Process of Obtaining Active Fraction by Column Chromatography

About 1.5 Kg of methanol extract of *Saxifraga ligulata* was suspended in 10 L of methanol and slurry was prepared with 4 Kg of silica gel (60-120 mesh). The column was packed in Chloroform:Methanol (80:20) with 10 kg of silica gel. The column was then eluted with 15 L of Chloroform:Methanol (80:20) (T3), 8 L of Chloroform:Methanol (60:40) (T2), 16 L of Chloroform:Methanol (50:50) (T1), 14 L of Chloroform:Methanol (25:75) (T5) and 15 L of Methanol (100) (T4) to obtain active fraction (Chloroform: Methanol 50:50) with the yield of 27% (405 g from 1.5 Kg).

Example 5

A Process of Obtaining Active Fraction by Direct Extraction from the Rhizomes of *Saxifraga ligulata*

A pilot scale experiment for the extraction of 2 kg of rhizomes of *Saxifraga ligulata* was carried out to obtain direct active fraction from the raw material in cost effective manner as follows.

About 2 kg each of raw material was placed in two different percolators

In the first percolator, 5 L of Chloroform:Methanol (80:20) solvent mixture was added and kept for 48 hours with occasional stirring. This extraction was repeated twice and the combined C:M (80:20) extractions were concentrated to dryness on a rotatory evaporator at optimum temperature to yield extract (TR-12).

The residual material from the first percolator was air dried and immersed with 5 L of Choom:Methanol (50:50) solvent mixture for 48 hours with occasional stirring. This extraction was repeated twice and the combined C:M (50:50) extractions were concentrated to dryness on a rotatory evaporator at optimum temperature to yield extract (TR-13).

In the second percolator, 5 L of Chloroform:Methanol (50:50) solvent mixture was added and kept for 48 hours with occasional stirring. This extraction was repeated twice and the combined C:M (50:50) extractions were concentrated to dryness on a rotatory evaporator at optimum temperature to yield extract (TR-14).

The residual material from the second percolator was air dried and immersed with 5 L of Choom:Methanol (80:20) solvent mixture for 48 hours with occasional stirring. This extraction was repeated twice and the combined C:M (80:20) extractions were concentrated to dryness on a rotatory evaporator at optimum temperature to yield extract (TR-15).

The residual material after shade drying was again extracted with 5 L of methanol by percolation method twice and the combined methanol extractions were concentrated to dryness on a rotatory evaporator at optimum temperature to yield extract (TR-16).

Example 6

Chemical Analysis of *Saxifraga ligulata* Extract

Thin Layer Chromatography was performed over pre-coated TLC plates (Merck) and samples of 50 μL, 100 μL (50 mg in 1 ml solution) were applied and run in the mobile phase of Methanol:Ethyl acetate:Acetic acid (75:24:0.1). The plates were then air dried and sprayed with 1% alcoholic $FeCl_3$ solution. A dark brown spots were visualized confirming the presence of phenolic compounds.

HPLC Analysis of *Saxifraga ligulata* Extract and Active Fractions

All samples from the extracts and fractions of *Saxifraga ligulata* were prepared at the concentration of 1 mg/ml in methanol (HPLC grade) as working standard. Other HPLC conditions are as follows:

| HPLC (Shimadzu) LC-8 with PDA detector | |
|---|---|
| Column: | Reverse Phase, C-18 |
| Mobile Phase: | 0.1% Phosphoric acid in Water:Acetonitrile (80:20) |
| Flow Rate: | 0.8 ml/min. |
| UV: | $\lambda_{max}$ 254 nm |

Example 7

Preparation of *Emblica officinalis* Extracts by Percolation Method

The shade dried fruits of *Emblica officinalis* were pulverized to a coarse powder and 3 kg each of the powdered material was placed in three percolators.

The first percolator containing 3 Kg of material was subjected to successive extractions with 10 L of n-hexane, 10 L of Chloroform, 10 L of Methanol and 10 L of Water. Each solvent extraction was repeated twice and concentrated to dryness on Rotatory evaporator at optimum temperature to yield n-Hexane extract (PH-01 A), Chloroform extract (PH-01 D), Methanol extract (PH-01G) and Water extract (PH-01 I).

The second percolator containing 3 Kg of material was subjected to successive extractions with 10 L of Chloroform, 10 L of Methanol and 10 L of Water. Each solvent extraction was repeated twice and combined extractions were concentrated to dryness on Rotatory evaporator at optimum temperature to yield Chloroform extract (PH-01 B), Methanol extract (PH-01 E) and Water extract (PH-01 H).

The third percolator containing 3 Kg of material was subjected to successive extractions with 10 L of Methanol and 10 L of Water. Each solvent extraction was repeated twice and combined extractions were concentrated to dryness on Rotatory evaporator at optimum temperature to yield Methanol extract (PH-01 C) and Water extract (PH-01 F).

Example 8

Preparation of Extract from *Cipadessa baccifera* by Percolation Method

The dried aerial parts of *Cipadessa baccifera* were pulverized to a coarse powder and 3 Kg each of powdered material was placed in three percolators. The first percolator containing 3 Kg of material was subjected to successive extractions with 10 L of n-hexane, 10 L of dichloromethane, 10 L of chloroform, 10 L of ethyl acetate, 10 L of methanol and 10 L of water. Each extraction was repeated twice and the combined extractions were concentrated to dryness on rotatory evaporator at optimum temperature and under reduced pressure to yield n-hexane extract (CP-01 A), dichloromethane extract (CP-01 B) chloroform extract (CP-01 C), ethyl acetate extract (CP-01 D), methanol extract (CP-01 E) and water extract (CP-01 F).

The second percolator containing 3 Kg of material was subjected to successive extractions with 10 L of acetone, 10 L of methanol and 10 L of water. Each extraction was repeated twice and the combined extractions were concentrated to dryness on rotatory evaporator at optimum temperature to yield acetone extract (CP-01 G), methanol extract (CP-01 H) and water extract (CP-01 I).

The third percolator containing 3 Kg of material was subjected to extraction with 10 L of double distilled water and the extraction was repeated twice. The combined extractions were concentrated to dryness on a water bath at optimum temperature to yield water extract (CP-01 J).

Example 9

Preparation of Herbal Composition for Under Eye Cream

| Under Eye Cream actives composition EC-01 | |
|---|---|
| *Saxifraga ligulata* Methanol extract | 45.00 g |
| *Emblica officinalis* Methanol extract | 35.00 g |
| *Cippadessa baccifera* Water extract | 20.00 g |

(for 100 g of actives composition)

Example 10

| Under Eye Cream actives composition EC-02 | |
|---|---|
| *Saxifraga ligulata* Active fraction (TR-1) | 55.00 g |
| *Emblica officinalis* Methanol extract | 25.00 g |
| *Cippadessa baccifera* Water extract | 20.00 g |

(For 100 g of actives composition)

Example 11

| Under Eye Cream actives composition EC-03 | |
|---|---|
| *Saxifraga ligulata* Active fraction (TR-2) | 45.00 g |
| *Emblica officinalis* Methanol extract | 35.00 g |
| *Cippadessa baccifera* Water extract | 20.00 g |

(For 100 g of actives composition)

Example 12

| Under Eye Cream actives composition EC-09 | |
|---|---|
| *Saxifraga ligulata* Active fraction (T1) | 43.47 g |
| *Emblica officinalis* Methanol extract | 34.80 g |
| *Cippadessa baccifera* Water extract | 21.73 g |

(For 100 g of actives composition)

Example 13

Antioxidant Activity of *Emblica officinalis* Extracts by DPPH Method

The free radical scavenging activity of the *Emblica* extract was measured in terms of hydrogen donating or radical-scavenging ability using the stable radical DPPH.

Reagents

1. DPPH 0.1 mM: A primary stock of 4 mg/ml was prepared, from this secondary stock was prepared by diluting primary stock 1:10 with ethanol.

2. Drug stock: 1 mg/ml stock of *Emblica* extracts in DM water was prepared.

Procedure

100 µl of 0.1 mM solution of DPPH in ethanol was added to 100 µl of extract solution in water at different concentrations (The stock sample solutions were serially diluted with respective solvents to obtain lower dilutions). Thirty minutes later, the absorbance was measured at 517 nm. Lower absorbance of the reaction mixture indicates higher free radical scavenging activity. Butylated hydroxy toluene (BHT) was used as standard. The capability to scavenge the DPPH radical was calculated using the following equation:

$$DPPH\ Scavenged\ (\%) = \frac{(A_{cont} - A_{test})}{A_{cont}} \times 100$$

Where, Acont is the absorbance of the control reaction and Atest is the absorbance in the presence of the sample of the extracts.

Figure 1:
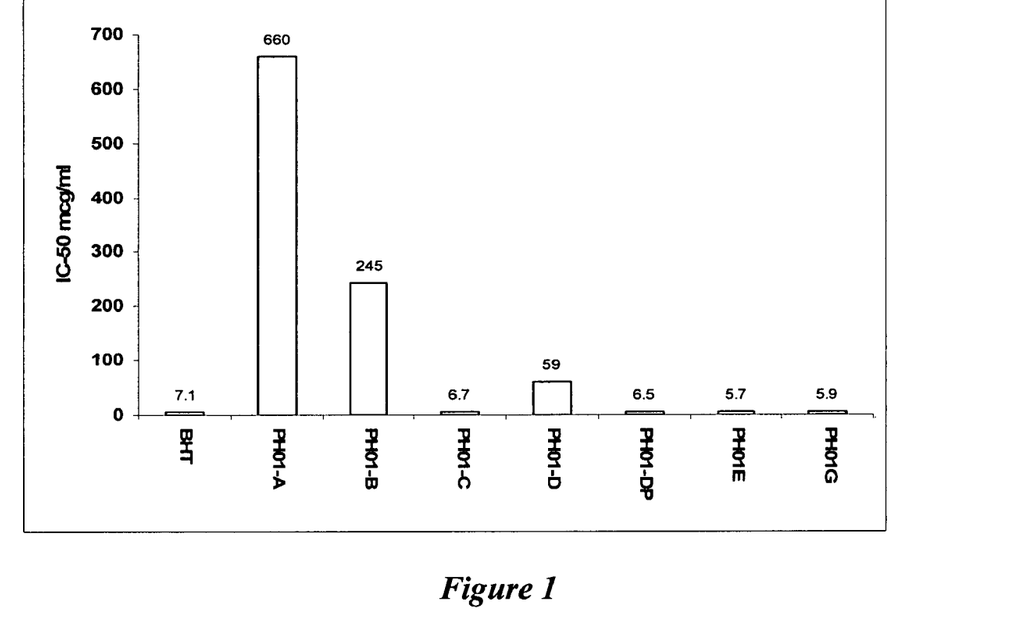
FIG. 1. DPPH radical scavenging activity of *Emblica officinalis* extracts ($IC_{50}$ values).
Figure 2:
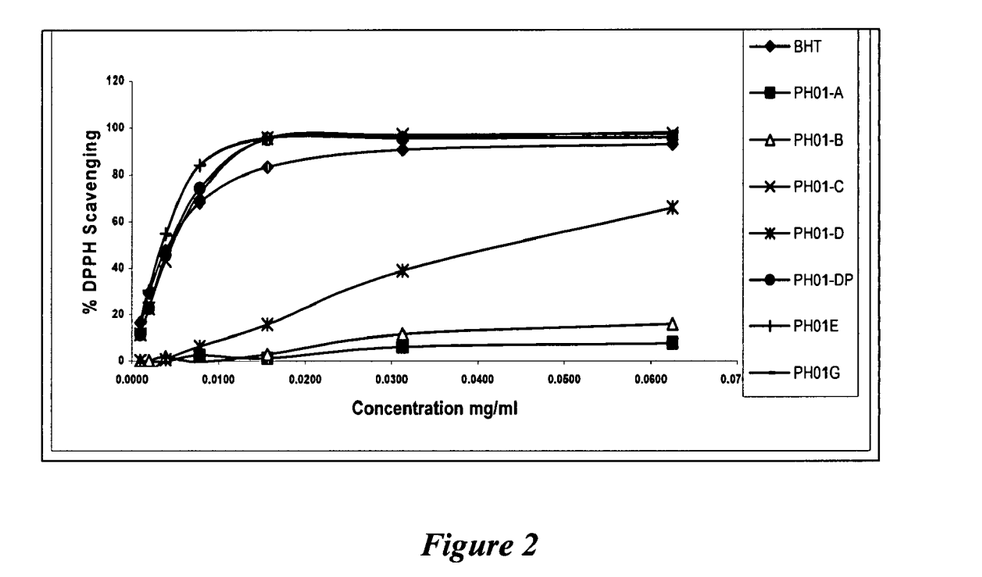
FIG. 2. DPPH radical scavenging activity of *Emblica officinalis* extracts (% of inhibition).
Figure 3:
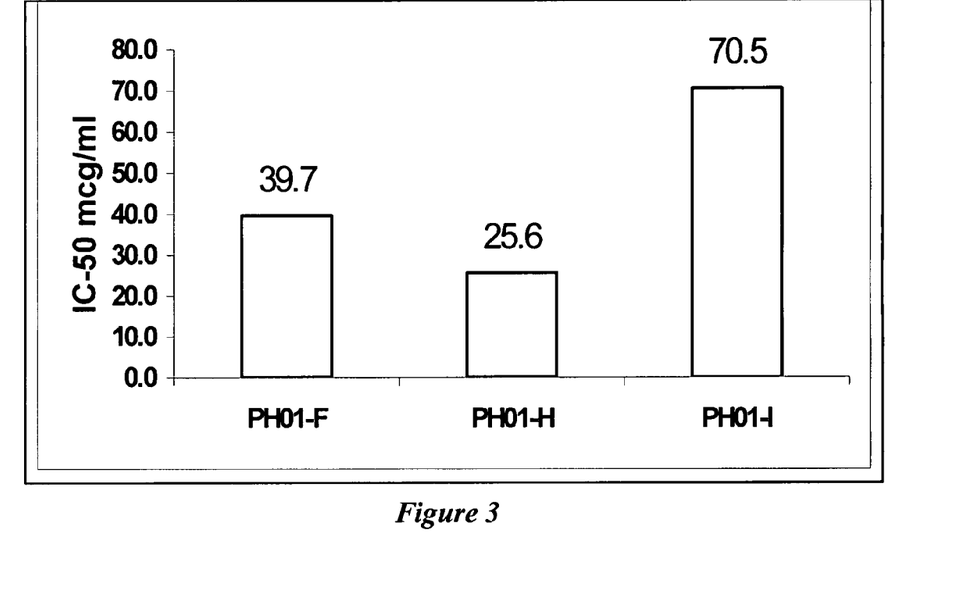
FIG. 3. DPPH radical scavenging activity of methanol extracts of *Emblica officinalis* ($IC_{50}$ values).
Figure 4:
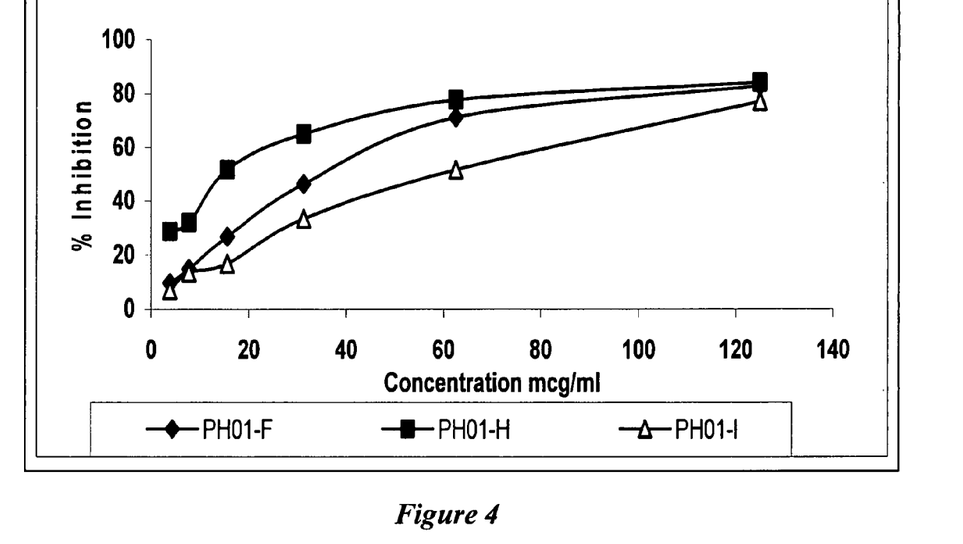
FIG. 4. DPPH radical scavenging activity of methanol extracts of *Emblica officinalis* (% of inhibition).

The antioxidant activity of the extract is expressed as $IC_{50}$. The $IC_{50}$ value is defined as the concentration (in µg/ml) of extracts that inhibits the formation of DPPH radicals by 50%. The activity results are summarized in FIGS. 1 and 4.

Example 14

Antioxidant Activity of UE Extract

All established methods for the measurement of total antioxidant activity are essentially inhibition methods: a free radical species is generated; there is an end point by which the presence of the radical is detected. The antioxidant activity of the added sample, which inhibits the end point by scavenging the radical, is measured. The Luminol/$H_2O_2$ system is reliable and practical for measuring total antioxidant activity. Luminol-dependent chemoluminescence was used for registration of reactive oxygen species (ROS). In the presence of antioxidant reductants and hydrogen donors the radical is quenched and chemiluminescence is inhibited.

Reagents and Materials

Luminol, Hydrogen peroxide-10 mM and Phosphate buffer: pH-7.

Example 15

The Total Antioxidant Activity Assay

Figure 5:
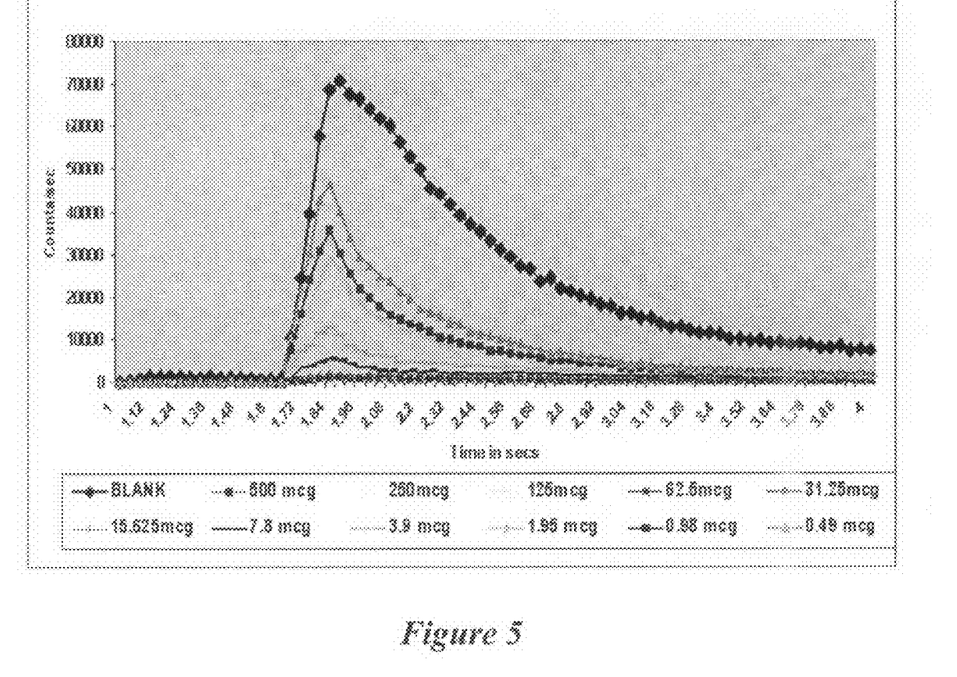
FIG. 5. Antioxidant activity of EC-09 extract (in vitro).
Figure 6:
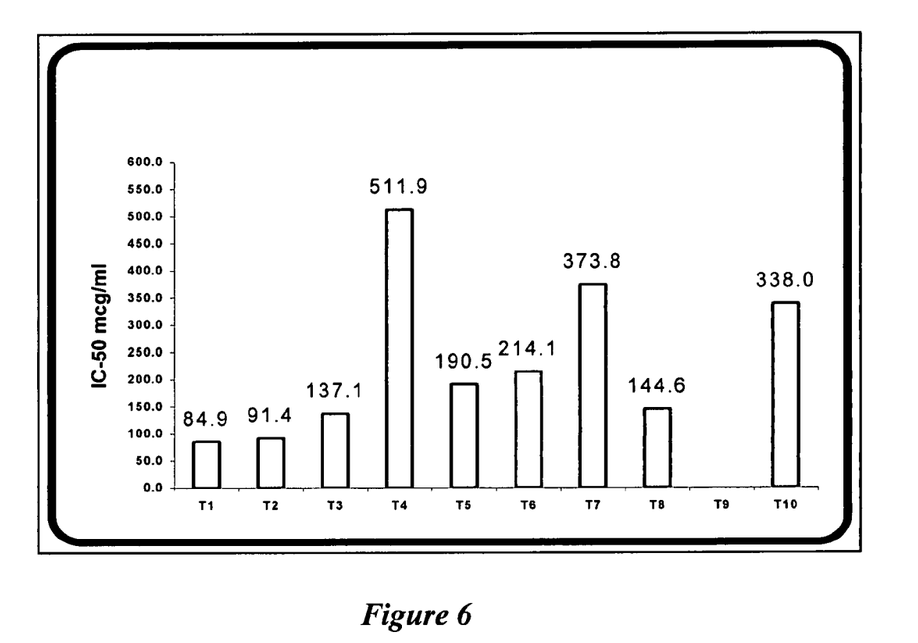
FIG. 6. In vitro Tyrosinase inhibitory activity of chromatographic fractions of methanol extract of *Saxifraga ligulata* ($IC_{50}$ values).
Figure 7:
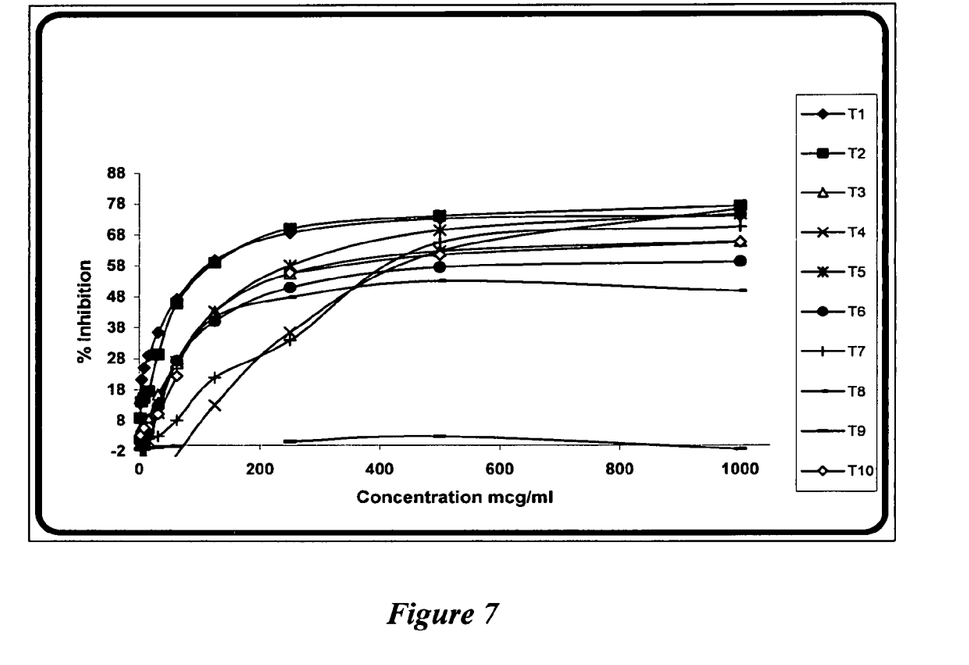
FIG. 7. In vitro Tyrosinase inhibitory activity of chromatographic fractions of methanol extract of *Saxifraga ligulata* (% of inhibition).
Figure 8:
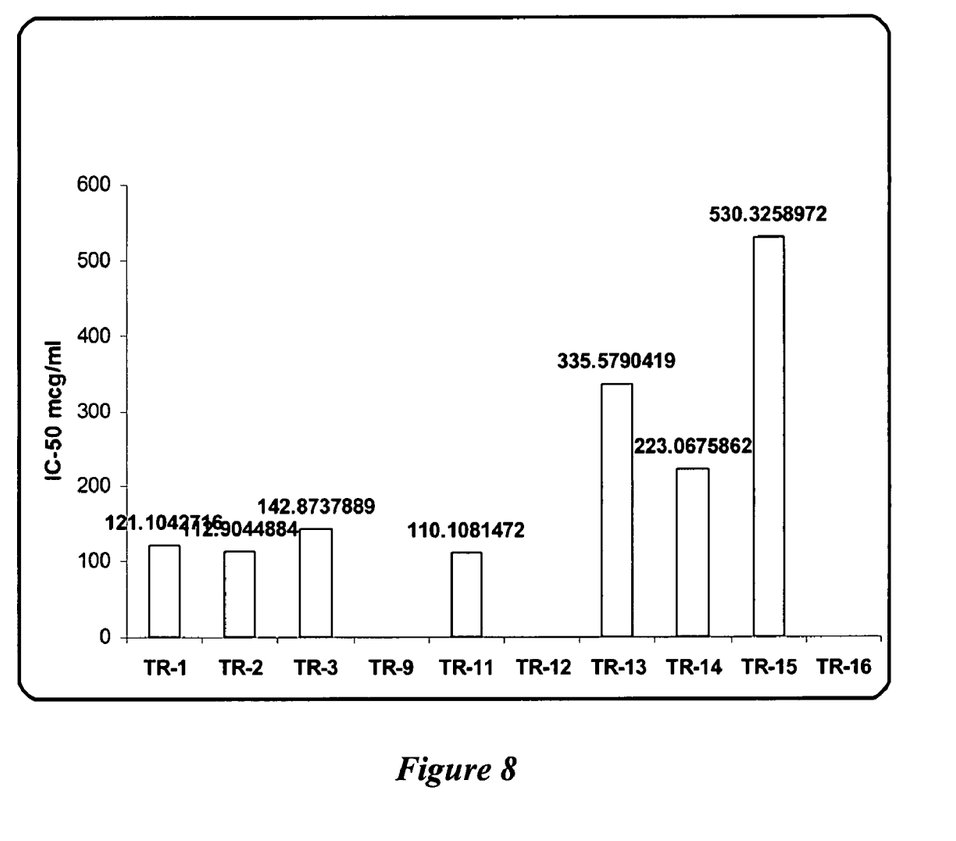
FIG. 8. In vitro Tyrosinase inhibitory activity of solvent-solvent fractions of methanol extract of *Saxifraga ligulata* ($IC_{50}$ values).
Figure 9:
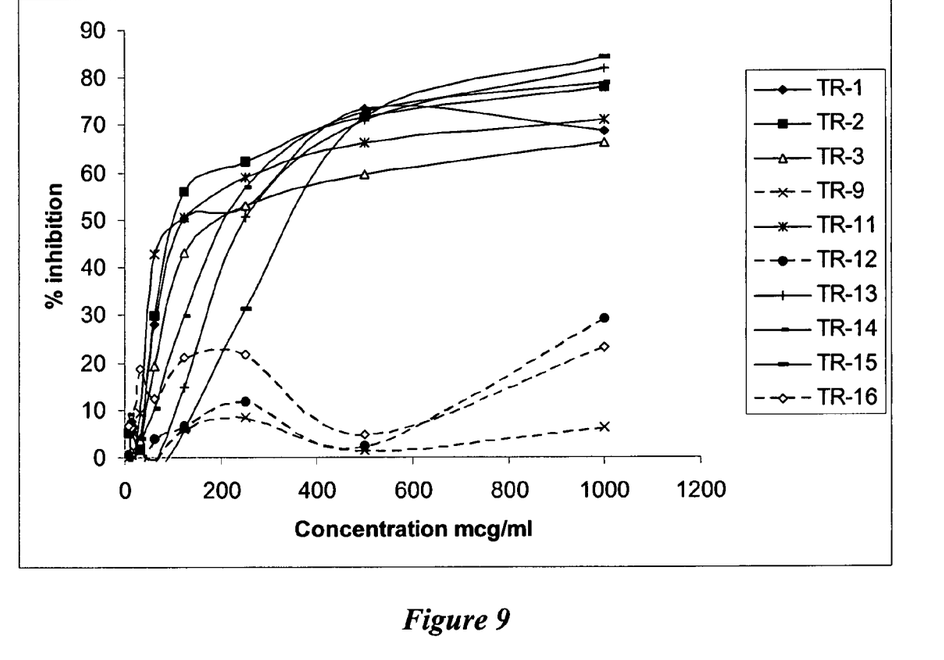
FIG. 9. In vitro Tyrosinase inhibitory activity of solvent-solvent fractions of methanol extract of *Saxifraga ligulata* (% of inhibition).
Figure 10:
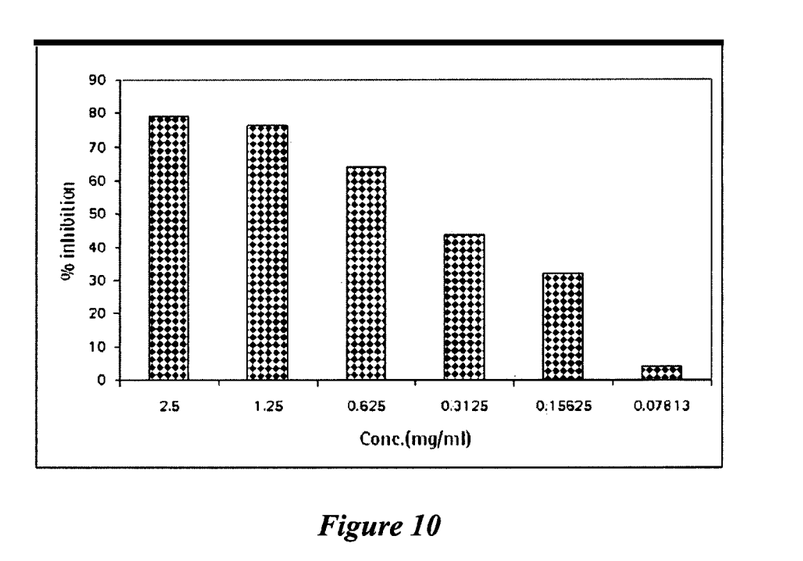
FIG. 10. Tyrosinase enzyme inhibitory activity of EC-09 extract (in vitro).

In a 96 well plate, each well was loaded with 100 µl of phosphate buffer. The test drug at different concentrations was added to each well except the first well, which was served as positive control. 100 µl of 1.0 mM luminol in 0.1 N NaOH was added to all the wells. Initial chemiluminescence i.e. before adding $H_2O_2$ was recorded. Accurately 25 µl of 10 mM $H_2O_2$ was added to the wells to initiate the reaction and chemiluminescence was recorded for 4-5 sec. in a flash mode. The results are summarized in FIG. 5.

Example 16

Tyrosinase Inhibitory Activity Assay

Reagents

1. Phosphate buffer 0.5 M, pH-6.8: Weigh 3.060 g of sodium dihydrogen phosphate and 3.479 g of disodium hydrogen phosphate, dissolve and make up the volume to 100 ml with DM water. Adjust the pH if required.
2. L-DOPA (2.55 mM): Weigh 10 mg of L-DOPA, dissolve and make up the volume to 20 ml in 0.5M Phosphate buffer, pH-6.8.
3. Tyrosinase Enzyme: Prepare 60 u/ml enzyme in 0.5 M Phosphate buffer, pH-6.8.
4. Sample solution: Stock of 1 mg/ml is prepared in 0.5 M Phosphate buffer pH-6.8.

Procedure

To 100 µl of the sample solution (for control and blank tubes taken 100 µl of buffer) 50 µl of Tyrosinase enzyme was added and the reaction was initiated by adding 50 µl of L-DOPA, (for blank tubes added buffer). The reaction kinetics were recorded for 30 min at 475 nm. The OD change was calculated.

$$\text{Tyrosinase Inhibition (\%)} = \frac{(A_{cont} - A_{test})}{A_{cont}} \times 100$$

Where, $A_{cont}$ is the absorbance change of the control reaction and $A_{test}$ is the absorbance change in the presence of the sample of the extracts.

The inhibitory activity of the extract is expressed as $IC_{50}$. The $IC_{50}$ value is defined as the concentration (in µg/ml) of extracts that inhibited the enzyme activity by 50%. The results are given in FIGS. 6-10.

Example 17

Hyaluronidase Inhibitory Activity

This assay was carried out in 96 well micro plate. Drug solutions were serially diluted with 0.02 M sodium phosphate buffer (pH 6.9) in the well and 30 µl of hyaluronic acid (1 mg/ml) was added as a substrate. Plate was read at 595 nm to record the initial reading. The mixture was incubated with freshly prepared hyaluronidase enzyme (30 µl, 200 IU/ml in 0.02 M sodium phosphate buffer with 1 mg BSA/ml) at 37° C. for 20 minutes. Then the reaction was stopped by adding 200 µl acid albumin solution (Acid Albumin Solution pH 3.72-3.78). It was allowed for 20 minutes at room temperature and read at 595 nm.

Example 18

Skin-Lightening Activity of UE Extract

Materials and Methods

DBA/2 mice of either sex weighing 20-25 grams were selected for the study. The animals were housed in polypropylene cages and were given free access to pelleted feed and water. A 12-hr light/dark cycle was maintained. The mice were divided into three groups, each comprising of six animals.

Procedure

Group I animals served as normal age matched controls with no exposure to UV light.

Group II animals were exposed to UV light for 20 minutes daily.

Group III animals were applied with UE cream on the dorsal region and exposed to UV light for 20 minutes daily.

Group IV animals were applied with competitor cream on the dorsal region and exposed to UV light for 20 minutes daily.

The mice were lightly anesthetized with ether and the hair on the back (dorsal region) was cleanly shaven. All the mice were exposed to UV light by using a UV sun lamp for 20 minutes daily, for duration of 15 days. The skin response was examined through out the study period. The degree of tanning was scored in the following grade and photographs were taken.

Figure 11:
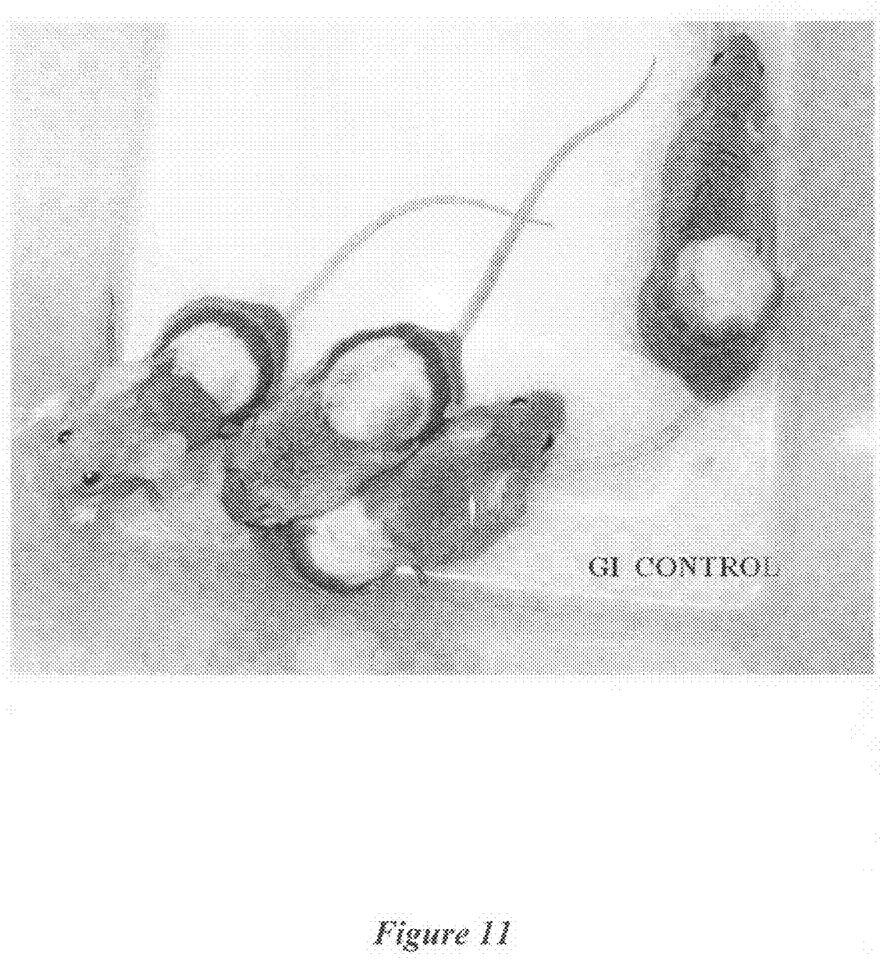
FIG. 11. Group I (Control) mice showing no melanin pigmentation.
Figure 12:
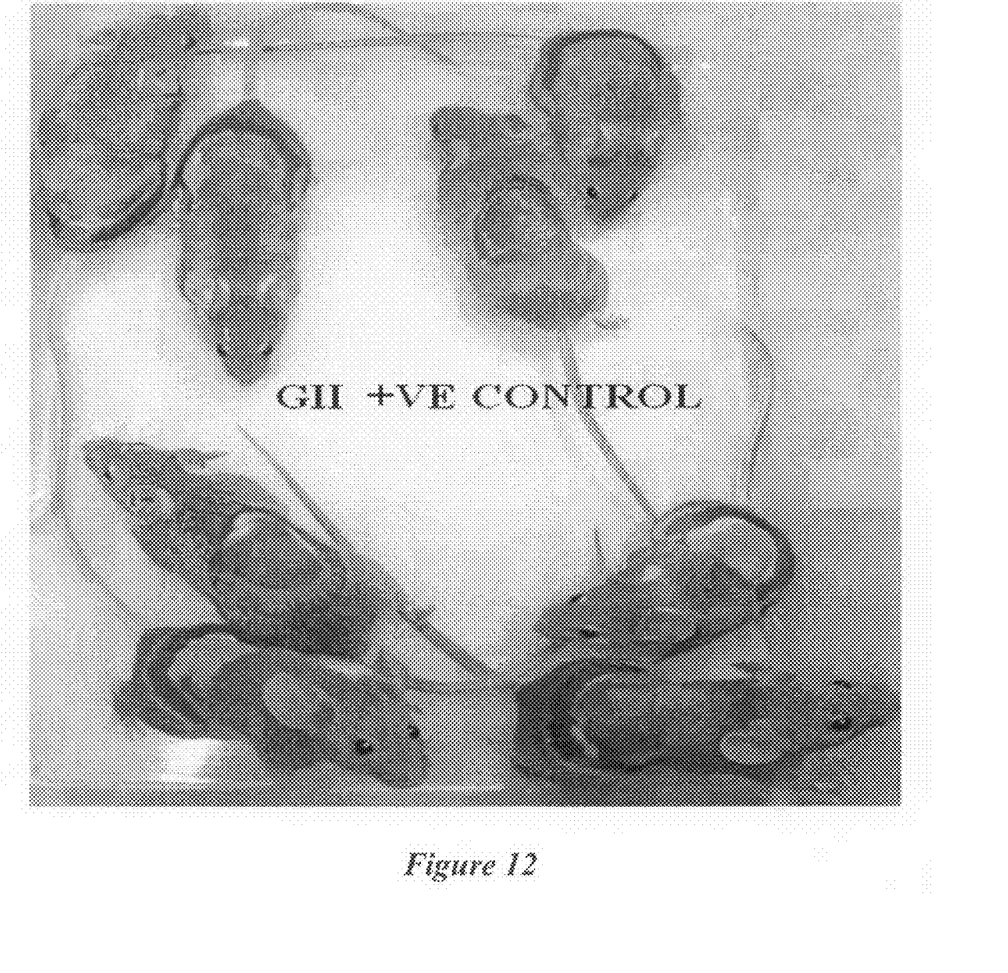
FIG. 12. Group II (Positive control) mice exposed to ultraviolet light showing high degree of melanin pigmentation.
Figure 13:
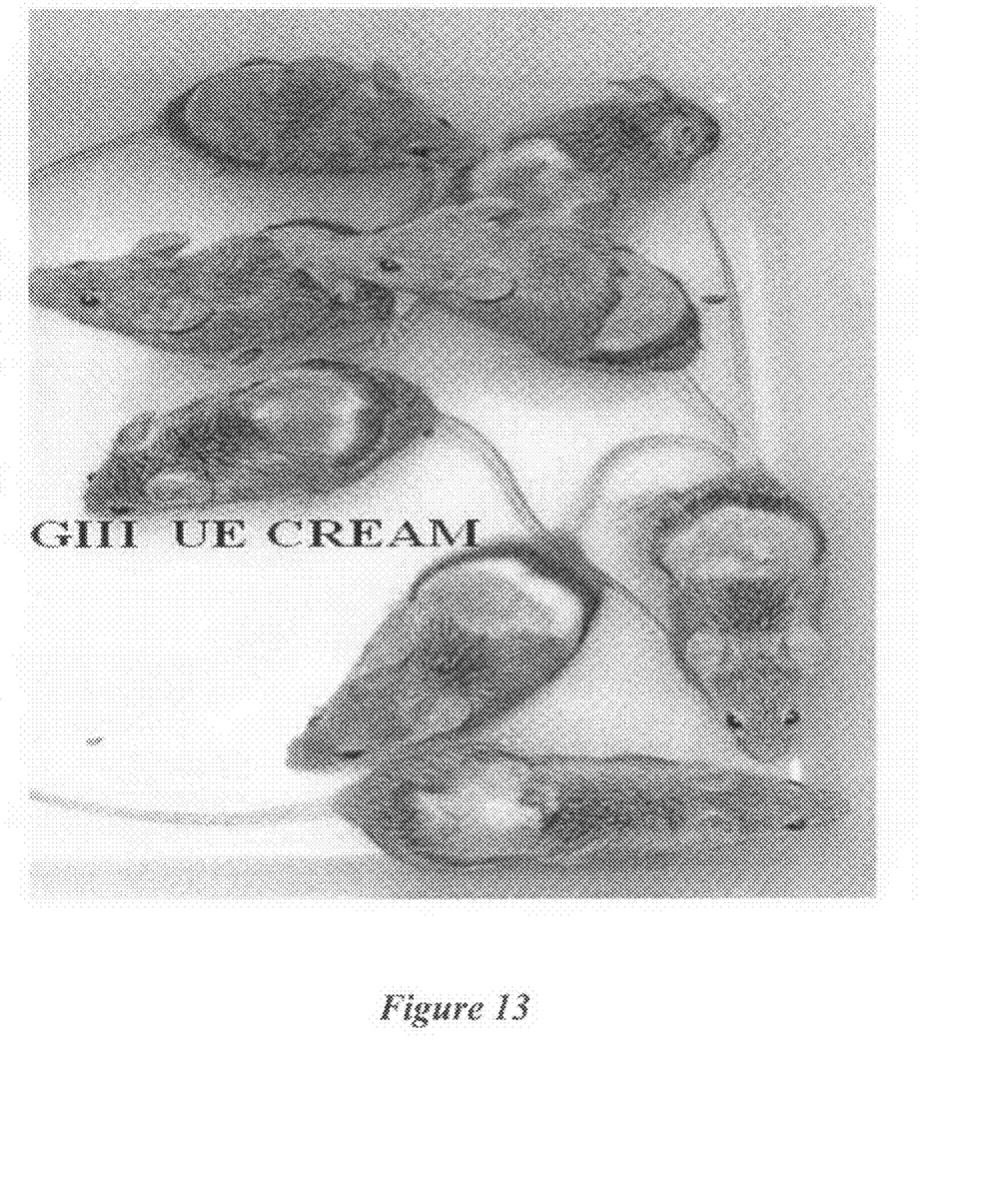
FIG. 13. Group III (Treated) mice treated with UE cream and exposed to UV light showing mild melanin pigmentation.

Exposure of mice skin to UV irradiation resulted in significant increase in melanin synthesis in Group II animals as compared to Group I animals (non UV irradiation). Daily application of UE cream offered a very good protection against UV induced melanin pigmentation (Group III) and was found to be almost equivalent to competitor's product (Group IV). The photographs of mice are given as FIG. 11 to 13.

Example 19

Clinical Trials of Under Eye Cream for Evaluation of Safety and Efficacy

To evaluate the dermal safety and efficacy of Under Eye Cream in humans, a clinical study was carried out among the outpatients in The Apollo Hospital Chennai. Twenty two healthy volunteers (3 male and 19 female) of age group 20 to 50 years were selected from the outpatient Cosmetology Clinic of Apollo Hospital Chennai for wrinkles under the eye, laxity of the muscles below the eye or dark black circles around the eye.

At the time of entry into the study, the following parameters—wrinkles under the eye, laxity, dark circles around the eye were assessed and scored on a scale of 0-3 as 0=None; 1=Mild; 2=Moderate and 3=Severe. Based on this, overall severity was assessed. They were then supplied with the treatment materials with instruction to apply two times per day below the eye for a period of 28 days. They were then followed at 15 day intervals. During each visit to the hospital, the signs and symptoms were assessed and scored as before. In addition, the refreshing effect of the cream, cleansing effect as well as soothing effect were scored on a scale of 0-3 as 0=None; 1=Mild; 2=Good and 3=Excellent. Erythema and edema if any were assessed and scored.

At the end of the study the patient was asked to give their overall impression about therapy by taking into account both the efficacy tolerability and safety of the formulation as follows:

- −1=Poor (The condition became worse)
- 0=Fair (Less than 50% relief from signs and symptoms)
- 1=Good (50 to 74% relief from signs and symptoms)
- 2=Very good (75 to 90% relief from signs and symptoms and
- 3=Excellent (More than 90% relief)

Figure 14:
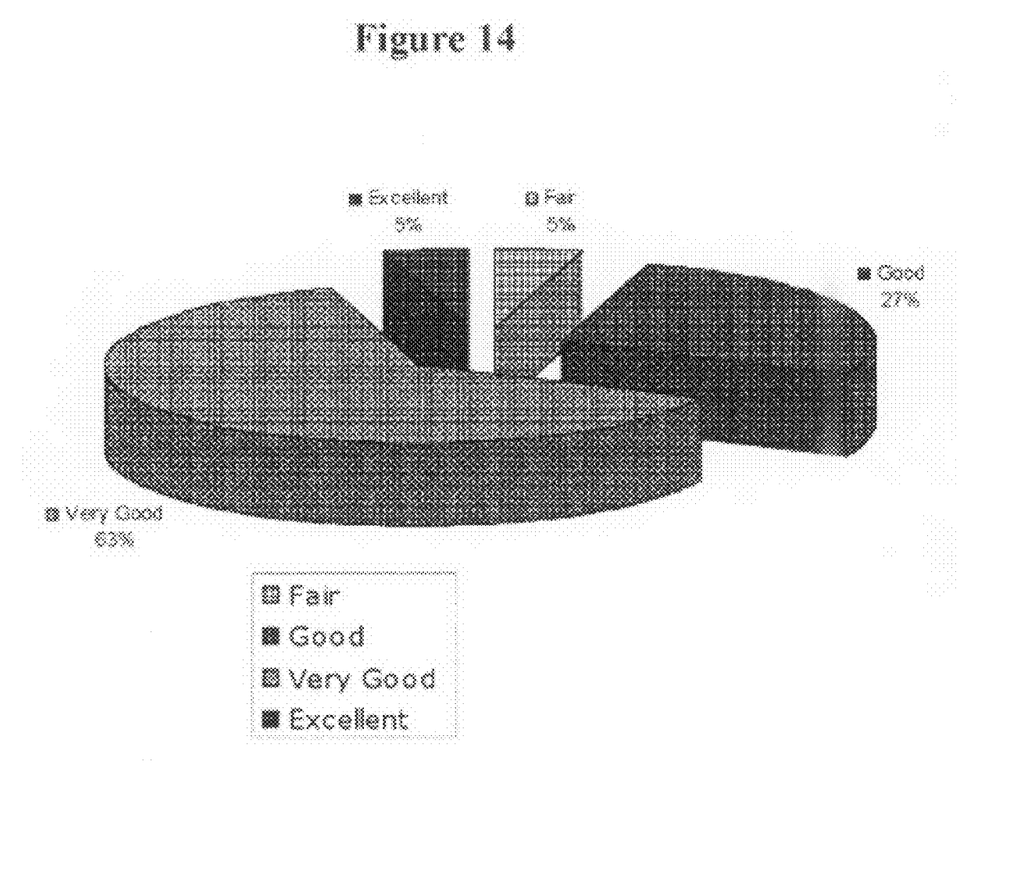
FIG. 14. Diagram showing opinion of patients on efficacy of under eye cream.

The overall impression about therapy is given in FIG. 14.

To evaluate the ocular safety, CT scan of the eye was done on all the 22 volunteers before commencement of the study and after completion of the study. CT study revealed no abnormality in any of the volunteers. The formulation was tolerated well by all the volunteers and none of the volunteers reported either erythema or pruritus.

Based on the above findings, it is concluded that The Under-Eye Cream developed from the present invention is safe and effective. However evaluations in larger number of patients with longer periods of follow-up are warranted.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

What is claimed is:

1. An herbal composition for application to skin around eyes comprising an extract obtained from rhizomes of the plant *Saxifraga ligulata* syn. *Bergenia ligulata*, an extract obtained from the aerial parts of the plant *Cipadessa baccifera* and an extract obtained from the fruits of the plant *Emblica officinalis* and a cosmeceutically acceptable excipient, wherein the extract of *Saxifraga ligulata* is a methanol extract or chloroform:methanol extract, the extract of *Cipadessa baccifera* is a water extract and the extract of *Emblica offcinalis* is a methanol extract.

2. The composition according to claim 1, wherein said extract of *Saxifraga ligulata* is obtained employing methanol.

3. The composition according to claim 1, wherein said extracts are in the ratio of 45 (*Saxifraga ligulata*): 35 (*Emblica officinalis*): 20 (*Cippadesa baccifera*).

4. The composition according to claim 1, wherein the composition is in the form of a topical composition selected from the group consisting of a cream, gel, lotion, oil, stick or spray.

5. A method for the treatment of a patient suffering from under eye dark circles, under eye wrinkles, under eye bags, a free radical damage of the skin around eye, hyper pigmentation around the eye, inflammation or puffiness around the eye, comprising applying the composition of claim 1 to said patient.

6. The method of claim 5 wherein said composition inhibits the enzyme Tyrosinase and the enzyme Hyaluronidase.

7. The method of claim 5, wherein the composition is applied after treatment for under eye dark circles, under eye wrinkles, under eye bags, a free radical damage of the skin around eye, hyper pigmentation around the eye, inflammation or puffiness around the eye with said composition.

8. A method of improving the skin around eyes of a patient comprising applying the composition of claim 1 to the patient.

* * * * *

UNITED STATES PATENT AND TRADEMARK OFFICE
CERTIFICATE OF CORRECTION

PATENT NO. : 7,785,637 B2
APPLICATION NO. : 11/811173
DATED : August 31, 2010
INVENTOR(S) : Mitra et al.

It is certified that error appears in the above-identified patent and that said Letters Patent is hereby corrected as shown below:

Title Page

At the face page, Item 54 (Title), after "CARING" please insert --FOR--.

At the face page under "Other Publications," Item (56); column 2, line 14, please delete ""Pharmacognistic" and insert therefore, --"Pharmacognostic--.

At column 1, line 2, after "CARING" please insert --FOR--.

At column 1, line 14-15, please delete "cosmecuticals." and insert therefore, --cosmeceuticals--.

At column 1, lines 50-52, below "bags." please delete "area. Over time, the septum surrounding the eyeball socket weakens, which causes the outer layer of fat within the socket to sink forward—resulting in pouches, or bags.".

At column 2, line 42, please delete "*mukurossi*" and insert therefore, --*mukorossi*--.

At column 3, lines 40-42, please delete "comprising n-hexane, dichloromethane, chloroform, ethyl acetate, acetone, methanol, ethyl alcohol and water or any combination thereof." and insert the same on col. 3, line 39, after "group" as a continuing paragraph.

At column 4, line 15, please delete "Chlroform:Methanol" and insert therefore --Chloroform:Methanol--.

At column 6, line 64, please delete "Hot-Soxlation" and insert therefore, --Hot-Soxhalation--.

At column 7, line 1, please delete "hot-soxlation" and insert therefore, --hot-soxhalation--.

At column 7, line 55, after "percolators" please insert --.--.

At column 7, line 63, please delete "Choom:Methanol" and insert therefore, --Chloroform:Methanol--.

Signed and Sealed this
Seventh Day of June, 2011

David J. Kappos
*Director of the United States Patent and Trademark Office*

CERTIFICATE OF CORRECTION (continued)
U.S. Pat. No. 7,785,637 B2

At column 8, line 8, please delete "Choom:Methanol" and insert therefore, --Chloroform:Methanol--.

At column 9, line 53, please delete "*Cippadessa*" and insert therefore, --*Cipadessa*--.

At column 9, line 64, please delete "*Cippadessa*" and insert therefore, --*Cipadessa*--.

At column 10, line 9, please delete "*Cippadessa*" and insert therefore, --*Cipadessa*--.

At column 10, line 21, please delete "*Cippadessa*" and insert therefore, --*Cipadessa*--.

At column 11, line 6, please delete "chemoluminescence" and insert therefore, --chemiluminescence--.

At column 11, line 42, please delete "0.5M" and insert therefore, --0.5 M--.

At column 12, line 55, please delete "FIG." and insert therefore, --FIGS.--.

At column 14, line 15, in Claim 1, please delete "*offcinalis*" and insert therefore, --*officinalis*--.

At column 14, line 17, in Claim 2, please delete "obtained employing methanol." and insert therefore, --a methanol extract.--.

At column 14, line 20, in Claim 3, please delete "*Cippadesa*" and insert therefore, --*Cipadessa*--.